US007101842B2

(12) United States Patent
Faulk

(10) Patent No.: US 7,101,842 B2
(45) Date of Patent: Sep. 5, 2006

(54) TARGETED DELIVERY OF DRUGS FOR THE TREATMENT OF PARASITIC INFECTIONS

(75) Inventor: W. Page Faulk, Indianapolis, IN (US)

(73) Assignee: Faulk Pharmaceuticals, Inc., St. Simons Island, GA (US)

( * ) Notice: Subject to any disclaimer, the term of this patent is extended or adjusted under 35 U.S.C. 154(b) by 166 days.

(21) Appl. No.: 10/477,992

(22) PCT Filed: May 16, 2002

(86) PCT No.: PCT/US02/11893

§ 371 (c)(1),
(2), (4) Date: Nov. 17, 2003

(87) PCT Pub. No.: WO02/091992

PCT Pub. Date: Nov. 21, 2002

(65) Prior Publication Data

US 2004/0161428 A1  Aug. 19, 2004

Related U.S. Application Data

(60) Provisional application No. 60/291,017, filed on May 16, 2001, provisional application No. 60/291,018, filed on May 16, 2001.

(51) Int. Cl.
*A61K 38/00* (2006.01)
*A61K 31/70* (2006.01)
(52) U.S. Cl. .................. 514/2; 514/8; 514/21; 514/34; 514/52; 530/300; 530/394
(58) Field of Classification Search .................... 514/8, 514/21, 34, 2, 52; 530/380, 392, 394, 395, 530/406, 410, 807, 828, 300; 536/6.4
See application file for complete search history.

(56) References Cited

U.S. PATENT DOCUMENTS

| | | | |
|---|---|---|---|
| 4,866,780 A | | 9/1989 | Mertz et al. |
| 4,886,780 A | | 12/1989 | Faulk |
| 4,895,714 A | | 1/1990 | Faulk |
| 5,000,935 A | | 3/1991 | Faulk |
| 5,268,165 A | * | 12/1993 | Hedlund et al. ............ 424/9.34 |
| 6,054,133 A | * | 4/2000 | Horwitz et al. ........... 424/248.1 |
| 6,183,723 B1 | * | 2/2001 | Seetharam et al. .......... 424/9.2 |

OTHER PUBLICATIONS

Faulk WP and Johnson PM. Immunological studies of human placentae. Identification and distribution of proteins in mature chorionic villi. Clin Exp Immunol 1977; 27: 365-375.
Faulk WP, Johnson PM, Dorling J and Temple A. Non-specific factors of resistance in human placentae. prot Biol Fluids 1976; 24: 139-142.

Johnson PM and Faulk WP. Immunological studies of human placentae: Identification and distribution of proteins in immature chorionic villi. Immunology 1978; 34: 1027-1035.
Faulk WP and Galbraith GMP. Trophoblast transferrin and transferrin receptors in the host-parasite relationship of human pregnancy. Proc R Soc Lond B 1979; 204: 83-97.
Hsi, BL, Yeh CJG and Faulk WP. Human amniochorion: Tissue-specific markers, transferrin receptors and histocompatibility antigens. Placenta 1982; 3: 1-12.
Yeh CJG, Hsi BL and Faulk WP. Histocompatibility antigens, transferrin receptors and extra-embryonic markers of human amniotic epithelial cells in vitro. Placenta 1983; 4: 361-368.
Galbraith GMP, Galbraith RM and Faulk WP. Transferrin binding by human lymphoblastoid cell lines and other transformed cells. Cell Immunology 1980; 49: 215-222.
Faulk WP, Hsi BL and Stevens PJ. Transferrin and transferrin receptors in carcinoma of the breast. Lancet 1980; ii: 390-392.
Yeh CJG, Taylor C and Faulk WP. Transferrin binding by peripheral blood mononuclear cells in human lymphomas, myelomas and leukemias. Vox Sanguinis 1984; 46: 217-223.
Faulk WP, Harats H and Berczi A. Transferrin receptor growth control in normal and abnormal cells. In: *Oxidoreduction at the Plasma Membrane*. vol. 1. (eds., FL Crane, JD Morre and H Low) CRC Press, Boca Raton, FL, 1990; pp. 205-224.
Yang DC, Wang F, Elliott RL and Head JF. Expression of transferrin receptor and ferritin H-chain mRNA are associated with clinical and histopathological prognostic indicators in breast cancer. Anticancer Res 2001; 21: 541-549.
Barnett D, Wilson GA, Lawrence AC and Buckley GA. Transferrin receptor expression in the leukaemias and lymphoproliferative disorders. Clin Lab Haematol 1987; 9: 361-70.
Whitney JF, Clark JM, Griffin TW, Gautam S and Leslie KO. Transferrin receptor expression in nonsmall cell lung cancer. Histopathologic and clinical correlates, Cancer 1995; 76: 20-25.
Recht L, Torres CO, Smith TW, Raso V and Griffin TW. Transferrin receptor in normal and neoplastic brain tissue: implications for brain-tumor immunotherapy. J Neurosurg 1990; 72: 941-945.
Sciot R, Paterson AC, van Eyken P, Callea F, Kew MC and Desmet VJ. Transferrin receptor expression in human hepatocellular carcinoma: an immunohistochemical study of 34 cases. Histopathol 1988; 12: 53-63.

(Continued)

*Primary Examiner*—Elli Peselev
(74) *Attorney, Agent, or Firm*—Rothwell, Figg, Ernst & Manbeck, P.C.

(57) ABSTRACT

Targeting agents such as transferrin and transcobalamin can be conjugated with anti-protozoan drugs for the treatment of protozoan infections. Any suitable anti-protozoan drug can be used, preferably the drug is selected from the group consisting of apoptosis inducing compounds, cytotoxic antibiotics, alkalating agents, plant toxins, and bacterial mutant toxins. The targeting agent is preferably coupled to the antiprotozoan drug by means of glutaraldehyde.

15 Claims, No Drawings

OTHER PUBLICATIONS

Seymour GJ, Walsh MD, Lavin MF, Strutton G and Gardiner RA. Transferrin receptor expression by human bladder transitional cell carcinomas. Urol Res 1987; 15: 341-344.

Lindholm ML, Lindberg LA, Vilja P, Puolakka VM, Nordling S, Schroder T and Schroder J. Expression of the human transferrin receptor in subrenal capsule assay in the mouse. J Surg Oncol 1988; 38: 57-62.

Hereiz HA and Bayoumi FA. Evaluation of diagnosis of ovarian malignancy using immunohistochemical technique. J Egyptian Public Hlth Assoc 1992; 67: 697-707.

Medeiros LJ, Picker LJ, Horning SJ and Warnke RA. Transferrin receptor expression by non-Hodgkin's lymphomas. Correlation with morphologic grade and survival. Cancer 1988; 61: 1844-1851.

Soyer HP, Smolle J, Torne R and Kerl H. Transferrin receptor expression in normal skin and in various cutaneous tumors. J Cutaneous Pathol 1987; 14: 1-5.

Lesley J, Hyman R, Schulte R and Trotter J. Expression of transferrin receptor on murine hematopoietic progenitors. Cell Immunol 1984; 83: 14-25.

Testa U, Pelosi E and Peschle C. The transferrin receptor. Crit Rev Oncogen 1993; 4: 241-276.

Bothwell TA, Charlton RW, Cook JD and Finch CA. *Iron Metabolism in Men*, Blackwell Scientific, Oxford, 1979.

Ponka P and Lok CN. The transferrin receptor: role in health and disease. Int J Biochem Cell Biol 1999; 31: 1111-1137.

Hamilton TA, Gray PW and Adams DO. Expression of the transferrin receptor on murine peritoneal macrophages is modulated by in vitro treatment with interferon gamma. Cell Immunol 1984; 89: 478-488.

Byrd TF and Horowitz MA. Interferon gamma-activated human monocytes downregulate transferrin receptors and inhibits the intracellular multiplication of *Legionella. pneumophila* by limiting the availability of iron. J Clin Invest 1989; 83: 1457-1465.

Kronke M, Leonard W, Depper JM and Greene WC. Sequential expression of genes involved in human T lymphocyte growth and differentiation J Exp Med 1985; 161: 1593-1598.

Galbraith RM and Galbraith GM. Expression of transferrin receptors on mitogen-stimulated human peripheral blood lymphocytes: relation to cellular activation and related metabolic events. Immunology 1983; 133: 703-710.

Neckers LM and Cossman J. Transferrin receptor induction in mitogen-stimulated human T lymphocytes is required for DNA synthesis and cell division and is regulated by interleukin 2, Proc Nat Acad Sci USA 1983; 80: 3494-3498.

Testa U, Kuhn L. Petrini M, Quaranta MT, Pelosi E and Peschle C. Differential regulation of iron regulatory element-binding protein(s) in cell extracts of activated lymphocytes versus monocytes-macrophages. J Biol Chem 1991; 266: 3925-3930.

Seiser C, Texieira S and Kuhn LC. Interleukin-2-dependent transcriptional and post-transcriptional regulation of transferrin receptor mRNA. J Biol Chem 1993; 268: 13,074-13, 080.

Neckers, LM, Yenokida G and James SP. The role of the transferrin receptor in human B lymphocyte activation. J Immunol 1984; 133: 2437-2441.

Neckers LM and Trepel JB. Transferrin receptor expression and the control of cell growth. Cancer Invest 1986; 4: 461-470.

Yeh CJG, Papamichall M and Faulk WP. Loss of transferrin receptors following induced differentiation of HL-60 promyelocytio leukemia cells. Exper Cell Res 1982; 138: 429-431.

Barker KA and Newburger PE. Relationship between the cell cycle and the expression c-myc and transferrin receptor genes during induced myeloid differentiation. Exper Cell Res 1990; 186: 1-5.

Klausner RD, Rouault TA and Harford JB. Regulating the fate of mRNA: the control of cellular iron metabolism. Cell 1993; 72: 19-28.

Haile DJ. Regulation of genes of iron metabolism by the iron-response proteins. Am J Med Sciences 1999; 318: 230-240.

Gatter KC, Brown G, Trowbridge IS, Woolston RE and Mason DY. Transferrin receptors in human tissues: their distribution and possible clinical relevance. J Clin Pathol 1983; 36: 539-545.

Faulk WP and Hunt JS. Human placentae: view from an immunological bias. Am J Reprod Immunol 1990; 21: 108-113.

Broadwell RD, Baker-Caims BJ, Friden PM, Oliver C and Villegas JC. Transcytosis of protein through the mammalian cerebral epithelium and endothelium. III. Receptor mediated transcytosis through the blood-brain barrier of blood-borne transferrin and antibody against transferrin receptor. Exp Neurol 1996; 142: 47-65.

Ponka P, Beaumont C and Richardson DR. Function and regulation of transferrin and ferritin. Seminars in Hematol 1998; 35: 35-54.

Sylvester SR and Griswold MD. The testicular iron shuttle A "nurse" function of the Sartoli cells. J Androl 1994; 15: 381-385.

Yeh CJG and Faulk WP. Killing of human tumor cells in culture with adriamycin conjugates of human transferrin. Clin Immunol Immunopath. 1984; 32: 1-11.

Yeh CJG, Taylor CG and Faulk WP. Targeting of cytotoxic drugs by transferrin receptors: Selective killing of acute myelogenous leukemia cells. Protides Biol Fluids 1984; 32: 441-444.

Berczi A, Barabas K, Sizensky JA and Faulk WP. Adriamycin conjuagtes of human transferrin bind transferrin receptors and kill K562 and HL60 cells. Arch Biochem Biophys 1993; 300: 356-363.

Lai BT, Gao JP and Lanka KW. Mechanism of action and spectrum of cell lines sensitive to a doxorubicin-transferrin conjugate. Cancer Chemother & Pharmacol 1998; 41: 155-160.

Kratz F, Beyer U, Roth T, Tarasova N, Collery P. Lechanault F, Cazabat A, Schumacher P, Unger C and Falken U. Transferrin conjugates of doxorubicin synthesis, characterization, cellular uptake, and in vitro efficacy. J Pharm Sciences 1998; 87: 338-346.

Tanaka T, Kaneo Y and Miyashita M. Synthesis of transferrin-mitomycin C conjugates as a receptor-mediated drug targeting system. Biol Pharm Bull 1996; 19: 774-777.

Sasaki K, Kohgo Y, Kato J, Kondo H and Niitsu Y. Intracellular metabolism and cytoxicity of transferrin-neocarzinostatin conjuagtes of differing molar ratios. Jpn J Cancer Res 1993; 84: 191-196.

Laske DW, Youle RJ and Oldfield EH. Tumor regression with regional distribution of the targeted toxin TF-CRM107 in patients with malignant brain tumors. Nature Med 1997; 3: 1362-1368.

Beyer U, Roth T, Schumacher P, Maier G, Unold A, Frahm AW, Fiebig HH, Unger C and Kratz F. Synthesis and in vitro efficacy of transferrin conjugates of the anticancer drug chlorambucil. J Med Chem 1998; 41: 2701-2708.

Bicamumpaka E and Page M. In vitro cytotoxicity of paclitaxel-transferrin conjugate on H69 cells. Oncol Reports 1998; 5: 1381-1383.

Lemieux P, Page M and Noel C. In vivo cytotoxicity and antineoplastic activity of a transferrin-daunorubicin conjuagte. In Vivo 1992; 6: 621-627.

Guo M, Sun H, McArdle HJ, Gambling L and Sadler PJ. Ti(IV) uptake and release by human serum transferrin and recognition of Ti(IV)-transferrin by cancer cells: understanding the mechanism of action of the anticancer drug titanocene dichloride. Biochem 2000; 39: 10023-10033.

Shah D and Shen WC. Transcellular delivery of an insulin-transferrin conjuagte in enterocyte-like Caco-2 cells. J Pharm Sciences 1996; 85: 1306-1311.

Drobyski WR, UI-Haq R, Majewski D and Chitambar CR, Modulation of in vitro and in vivo T-cell responses by transferrin-gallium and gallium nitrate. Blood 1996; 88: 3056-3064.

Hoshino T, Misaki M, Yamamoto M, Shimizu H, Ogawa Y and Toguhi H. In vitro cytotoxicities and in vivo ditribution of transferrin-platinum(II) complex. J Pharm Sciences 1995; 84: 216-221.

Ippoliti R, Ginobbi P, Lendaro E, D'Agostino I, Ombres D, Benedetti PA, Brunori M and Citro G. The effect of monensin and chloroquine on the endocytosis and toxicity of chioneric toxiris. Cell Mol Life Sci 1998; 54: 866-875.

Kratz F, Hartmann F, Keppler B and Messor L. The binding properties of two antitumor ruthenium(III) complexes to apotransferrin. J Biol Chem 1994; 269: 2581-2588.

Park E, Starzyk RM, McGrath JP, Lee T, George J, Schutz AJ, Lynch P and Putney SD. Production and characterization of fusion proteins containing transferrin and nerve growth factor. J Drug Targeting 1998; 6: 53-64.

Ali SA, Joao HC, Hammerschmid F, Eder J and Steinkasserer A. Transferrin Trojan Horses as a rational approach for biological delivery of therapeutic peptide domains. J Biol Chem 1999; 274: 24066-24073.

Peters K and Richards FM. Chemical cross-linking: reagents and problems in studies of membrane structure. Annu Rev Biochem 1977; 46: 523-551.

Rhodes J. Evidence for an intercellular covalent reaction essential in antigen-specific T cell activation. J Immunol 1989; 143: 1482-1489.

Greenfield RS, Kaneko T, Daues A, Edson MA, Fitzgerald KA, Olech LJ, Grattan JA, Spitalny GL and Braslawsky GR. Evaluation in vitro of adriamycin immunoconjugates synthesized using an acid-sensitive hydrazone bond. Cancer Res 1990; 50: 6600-6607.

Braslawsky GR, Edson MA, Pearce W, Kaneko T and Greenfield RS. Antitumor activity of adriamycin (hydrazone-linked) immunoconjugates compared with free adriamycin and specificity of tumor cell killing. Cancer Res 1990; 50: 6608-6614.

O'Keefe DO and Draper RK. Characterization of a transferrin-diphtheria toxin conjugate. J Biol Chem 1985; 260: 932-937.

Neidle S, Pearl LH and Skelly JV. DNA structure and perturbation by drug binding Biochem J 1987; 243: 1-13.

Tritton TR Cell surface actions of adriamycin. Pharmacol & Therapeutics 1991: 49: 293-309.

Maestre N, Tritton TR, Laurent G and Jaffrezou JP. Cell surface-directed interaction of anthracyclines leads to cytotoxicity and nuclear factor kappaB activation but not apoptosis signaling. Cancer Res 2001; 61: 2558-2561.

Fong WF, Lam W, Yang M and Wong JT-F. Partial synergism between dextran-conjugated doxorubicin and cancer drugs on the killing of multidrug resistant KB-V1 cells. Anticancer Res 1996; 16: 3773-3778.

Barabas K, Sizensky JA and Faulk WP, Transferrin conjugates of adriamycin are cytotoxic without intercalating nuclear DNA. J Biol Chem 1992; 267: 9437-9442.

Faulk WP, Barabas K, Sun IL and Crane FL. Transferrin-adriamycin conjuagtes which inhibit tumor cell proliferation without interaction with DNA inhibit plasma membrane oxidoreductase and proton release in K562 cells. Biochem Int 1991; 25: 815-822.

Berczi A, Ruthner M, Szuts V, Fritzer M, Schweinzer E and Goldenberg H. Influence of conjugation of doxorubicin to transferrin on the iron uptake by K562 cells via receptor-mediated endocytosis. Euro J Biochem 1993; 213: 427-436.

Barabas K, Sizensky J and Faulk WP. Evidence in support of the plasma membrane as the target transferrin-adriamycin conjuagtes in K562 cells. Am J Reprod Immunol 1991; 25: 120-124.

Szuts V, Berczi A, Schweinzer E and Goldenberg H. Binding of doxorubicin-conjuagted transferrin to U937 cells. J Receptor Res 1993; 13: 1041-1054.

Ruthner M, Berczi A. and Goldenberg H. Interaction of a doxorubicin-transferrin conjugate with isolated transferrin receptors. Life Sci 1994; 54: 35-40.

Sainte-Marie J, Lafont V, Pecheur EI, Favero J, Philippot JR and Bienvenue A. Transferrin receptor functions as a signal-transduction molecule for its own recycling via increases in the internal Ca++ concentration. Euro J Biochem 1997; 250: 689-697.

Klausner RD, vanReuswoude J, Ashwell G, Kempf C, Schechter AN, Dean A and Bridges K. Receptor-mediated endocytosis of transferrin in K562 cells. J Biol Chem 1983; 258: 4715-4724.

Richardson DR and Ponka P. The molecular mechanisms of a metabolism and transport of iron in normal and neoplastic cells. Biochim Biophy Acta 1997; 1331: 1-40.

Baker MA and Lawen A. Plasma membrane NADH-oxidase system: a critical review of the structural and funotional data. Antioxidants & Redox Signaling 2000; 2: 197-212.

Sun IL, Navas P, Crane FL, Morre DJ and Low H. NADH-diferric transferrin reductase in liver plasma membranes. J Biol Chem 1987; 262: 15915-15921.

Sun IL, Navas P, Crane FL, Morre DJ and Low H. Diferric transferrin reductase in the plasma membrane is inhibited by adriamycin. Biochem Int 1987; 14: 119-127.

Faulk Wp, Harats H, McIntyre JA, Berczi A, Sun IL and Crane FL. Recent advances in cancer research: Drug targeting without the use of monoclonal antibodies. Am J Reprod Immunol 1989; 21: 151-154.

Morre DJ, Kim C, Paulik M, Morre DM and Faulk WP. Is the drug-response NADH- oxidase of the cancer cell plasma membrane a molecular target for adriamycin? Bioenerg Biomembr 1997; 29: 269-280.

Sun IL, Sun EE, Crane FL, Morre DJ and Faulk WP. Inhibition of transplasma membrane electron transport by transferrin-adriamycin conjugates. Biochim Biophy Acta 1992; 1105: 84-88.

Crane FL, Low H, Sun IL, Morre DJ and Faulk WP. Interaction between oxidoreductase, transferrin receptor and channels in the plasma membrane. In: *Growth Factors from Genes to Clinical Applications* (eds, VR Sara, K Hall and H Low) Raven Press, New York, 1990; pp. 228-239.

Hileti D, Panayiotidis P and Hoffbrand V. Iron chelators induce apoptosis in proliferating cells. Brit J Haetnatol 1995; 89: 181-187.

Leardi A, Caraglia M, Selleri C, Pepe S, Pizzi C, Notaro R, Fabbrocini A, De Lorenzo S, Musico M, Abbruzzese A, Bianco A and Tagliaferri P. Desferioxamine increases iron depletion and apoptosis induced by ara-C of human myeloid leukemic cells. Brit J Haematol 1998; 102: 746-752.

Barabas K, Miller SJ and Faulk WP. Regulation of transferrin receptor mRNA stability in drug-sensitive and drug-resistant cancer cells. To be submitted for publication, 2003.

Hentze MW and Kuhn LC. Molecular control of vertebrate iron-metabolism. mRNA-based regulatory circuits operated by iron, nitric oxide and oxidative stress. Proc Natl Acad Sci USA 1996; 93: 8175-8182.

Pantapoulos K and Hentze MW. Rapid responses to oxidative stress mediated by iron regulatory protein. EMBO J 1995; 14: 2917-1924.

Wardrop SL, Watts RN and Richardson DR. Nitrogen monoxide activates iron regulatory protein 1 RNA-binding activity by two possible mechanisms: effect on the 4Fe-4S cluster and iron mobilization from cells. Biochemistry 2000; 39: 2748-2758.

Eiseristein RS. Iron regulatory proteins and the molecular control of mammalian iron metabolism Annu Rev Nutr 2000; 20: 627-662.

Richardson DR, Naumannova V, Nagy E and Ponka P. The effect of redox-related species of nitrogen monoxide on transferrin and iron uptake and cellular proliferation of erythroleukemia (K562) cells. Blood 1995; 86: 3211-3219.

Kim S and Ponka P. Effects of interferon-gamma and lipopolysaccharide on macrophage iron metabolism are mediated by nitric oxide-induced degradation of iron regulatory protein 2. J Biol Chem 2000; 275: 6220-6226.

Nestel FP, Green RN, Kickian K, Ponka P and Lapp WS. Activation of macrophage cytostatic effector mechanisms during acute graft-versus host disease: release of intracellular iron and nitric oxide-mediated cytostasis. Blood 2000; 96: 1836-1843.

Kim S and Ponka P. Control of transferrin receptor expression via nitric oxide-mediated modulation of iron-regulatory protein 2. J Biol Chem 1999; 274: 3303 5-33042.

Laske DW, Ilercil O, Akbasak A, Youle RJ and Oldfield EH. Efficacy of direct intratumoral therapy with targeted protein toxins for solid human gliomas in nude mice. J Neurosurg 1994; 80: 520-526.

Singh M, Atwal H and Micetich R. Transferrin directed delivery of adriamycin to human cells. Anticancer Res 1998; 18(3A): 1423-1427.

Sato Y, Yamauchi N, Takahashi M, Sasaki K, Fukaura J, Neda H, Fujii S, Hirayma M, Itoh Y, Koshita Y, Kogawa K, Kato Sakamaki S and Niitsu Y. In vivo gene delivery to tumor cells by transferrin-streptavidin-DNA conjugate. FASEB Journal 2000; 14: 2108-2118.

Oldfield EH and Youle RJ. Immunotoxins for brain tumor therapy. Cur Top Microbiol Immunol 1998; 234: 97-114.

Kohgo Y, Kato J, Sasaki K and Kondo H. Targeting chemotherapy with transferrin-neocarzinostatin. Japanese J Cancer Chemotherapy 1988; 15: 1072-1076.

Faulk WP, Taylor CG, Yeh G and McIntyre JA. Preliminary clinical study of transferrin-adriamycin conjugate for drug delivery to acute leukemia patients. Mol Biother 1990; 2: 57-60.

Laske DW, Morrison PF, Lieberman DM, Carthesy ME, Reynolds JC, Stewart Henney PA, Koong SS, Cummins A, Paik CH and Oldfield EH. Chronic interstitial infusion of protein to primate brain: determination of drug distribution and clearance with single-photon emission computerized tomography imaging. J Neurosurg 1997; 87: 586-594.

Marbeuf-Gueye C, Ettori D, Priebe W, Kozlowski H and Garnier-Suillerot A. Correlation between the kinetics of anthracycline uptake and the resistance factor in cancer cells expressing the multidrug resistance protein or the P-glycoprotein. Biochem Biophy Acta 1999; 1450: 374-384.

Fritzer M, Barabas K, Szuts V, Berczi A, Szekeres T, Faulk WP and Goldenberg H. Cytotoxicity of a transferrin-adriamycin conjugate to anthracyloine resistant cells. Int J Cancer 1992; 52: 619-623.

Hatano T, Ohkawa K and Matsuda M. Cytotoxic effect of the protein-doxorubicin conjugates on the multidrug-resistant human myelogenous leukemia cell line, K562, in vitro. Tumor Biology 1993; 14: 288-294.

Lemieux P and Page M. Sensivity of multidrug-resistant MCF-7 cells to a transferrin-doxorubicin conjugate. Anticancer Res 1994; 14(2A): 397-403.

Fritzer M, Szekeres T, Szuts V, Jraayam HN and Goldenberg H. Cytotoxic effects of a doxorubicin-transferrin conjugate in multidrug-resistant KB cells. Biochem Pharm 1996; 51: 489-493.

Wang F, Jiang X, Yang DC, Elliot RL and Head JF. Doxorubicin-gallium-transferrin conjugate overcomes multidrug resistance: evidence for drug accumulation in the nucleus of drug resistant MCF-7/ADR cells. Anticancer Res 2000; 20: 799-808.

Soma CE, Dubernet C and Barratt G. Ability of doxorubicin-loaded nanoparticles to overcome multidrug resistance of tumor cells after their capture by macrophages. Pharm Res 1999; 16: 1710-1716.

Mazel M, Clair P, Rousselle C, Vidal P, Schermann J-M, Mathieu D and Temsamani J. Doxorubicin-peptide conjugates overcome multidrug resistance. Anti-Cancer Drugs 2001; 12: 107-116.

Anderson BF, Baker HM, Norris GE, Rumball SV and Baker EN. Apolactoferrin structure demonstrates ligand-induced conformational change in transferrins. Nature 1990; 344: 784-787.

Baker EN. Structure and reactivity of transferrin. Adv Inorg Chem 1994; 41: 389-463.

Harris WR. Equilibrium constants for the complexation of metal iron by serum transferrin. Adv Exp Med & Biol 1989; 249: 67-93.

Li H, Sadler PJ and Sun H. Unexpectedly strong binding of a large metal iron ($Bi^{3+}$) to human serum transferrin. J Biol Chem 1996; 271: 9483-9489.

Battistuzzi G, Calzolai L, Messori L and Sola M. Metal-induced conformational heterogeneity of transferrin: a spectroscopic study of indium (III) and other metals (III)-substituted transferrin. Biochem Biophys Res Com 1995; 206: 161-170.

Kubal G, Mason AB, Patl SU, Sadler PJ and Woodworth RC. Oxalate- and $Ga^{3+}$-induced structural changes in human transferrin and its recombinant N-lobe. $^1H$ NMR detection of preferential C-lobe $Ga^{3+}$binding. Biochem 1993; 32: 3387-3395.

Grossman JG, Neu M, Evans RW, Lindley PF, Appel H and Hasnain SS. Metal-induced conformational changes in transferrins. J Mol Biol 1993; 229: 585-590.

Sun H, Li H, Mason AB, Woodworth RC and Sadler PJ. N-lobe versus C-lobe complexation of bismuth by human transferrin. Biochem J 1999; 337: 105-111.

Dobson CB, Graham J and Itzhaki RF. Mechanism of uptake gallium by human neuroblastoma cells and effects of gallium and aluminum on cell growth, lysosornal protease, and choline acetyl transferase activity. Exp Neurol 1998; 153: 342-350.

Abreo K, Jangula J, Jain SK, Sella M and Glass J. Aluminum uptake and toxicity in cultured mouse hepatocytes. J Am Soc Nephrol 1991; 1: 1299-1304.

Sun H, Li H, Mason AB, Woodworth RC and Sadler PJ. Competitive binding of bismuth to transferrin and albumin in aqueous solution and in blood plasma. J Biol Chem 2001; 276: 8829-8835.

Gallori E, Vettori C, Alessio E, Vilchez FG, Vilaplana R, Orioli P, Casini A and Messori L. DNA as a possible target for antitumor ruthenium complexes. Arch Biochem Biophy 2000; 376: 156-162.

Ward SG and Taylor RC. In, Metal-Based Anti-Tumor Drugs (Gielen MF, Ed) 1988, pp. 1-54, Fruend Publishing House Ltd., London.

Kubal G and Sadler PJ. Sequential binding of aluminum (3+) to the C- and N-lobe of human serum transferrin detected by $^1H$ NMR spectroscopy. J Am Chem Soc 1992; 114: 1117-1118.

Kubal G, Mason Ab, Sadler PJ, Tucker A and Woodworth RC. Uptake of $Al^{3+}$into the N-lobe of human serum transferrin. Biochem J 1992; 285: 711-714.

Van Rensburg SJ, Carstens ME, Potocnik FCV and Taljaard JJF. The effect of iron and aluminum on transferrin and other serum proteins as revealed by isoelectric focusing gel electrophoresis. Annals NY Acad Sci 2000; 903: 150-155.

Kratz F, Hartmann M, Keppler B and Messori L. The binding properties of two antitumor ruthenium (III) complexes to apotransferin. J Biol Chem 1994; 269: 2581-2588.

Guo M, Sun H, McArdle JH, Gambling L and Sadler PJ. $Ti^{IV}$ uptake and release by human serum transferrin and recognition of $Ti^{IV}$-transferrin by cancer cells: understanding the mechanism of action of the anticancer drug titanocene dichloride. Biochem 2000; 39: 10023-10033.

Roskams AJ and Cosmor JR. Aluminum access to the brain: a role for transferrin and its receptor. Proo Natl Acad Sci USA 1990; 87: 9024-9027.

Knorr GM and Chitamber CR. Gallium-pyridoxal isonicotinoyl hydrazone (Ga-PIH), a novel cytotoxic gallium complex. A comparative study with gallium nitrate. Anticancer Res 1998; 18 (3A): 1733-1737.

Kasai K, Hori MT and Goodman WG. Transferrin enhances the antiproliferative effect of aluminum on osteoblast-like cells. Am J Physiol 1991; 260 (4Pt1): E537-543.

McGregor SJ, Naves ML, Birly AK, Russell NH, Halls D, Junor BJ and Brock JH. Interaction of aluminum and gallium with human lymphocytes: the role of transferrin. Biochim Biophys Acta 1991; 1095: 196-200.

Abreo K and Glass J. Cellular, biochemical, and molecular mechanisms of aluminium toxicity. Nephrol Dial Transplant 1993; 8 Suppl 1: 5-11.

Kratz F, Mulinacci N, Messori L, Bertini I and Keppler BK. In, Metal Ions in Biology and Medicine, vol. 2, pp. 69-74, John Libbey Limited Eurotext, Paris.

WiSniewski MZ, Wietrzyk J and Opolski A. Novel Ru(III), Rh(III), Pd(II) and Pt(II) complexes with ligands incorporating azole and pyrimidine rings. I. Antiproliferative activity in vitro. Arch Immunolog Therap Exper 2000; 48: 51-55.

Frasca DR, Gehrig LE and Clarke MJ. Cellular effects of transferrin coordinated to. J Inorg Biochem 2001; 83: 139-149.

Whelan HR, Williams MB, Bijic DM, Flores RE, Schmidt MH, McAuliffe TL and Chitambar CR. Gallium nitrate delays the progression of microscopic disease in a human medulloblastoma murine model. Ped Neurol 1994; 11: 44-46.

Ganot PO. Metabolism and possible health effects of aluminum. Envir Hlth Perspect 1986; 65: 363-441.

Keppler BK, Berger MR, and Heim ME. New tumor-inhibiting metal complexes. Cancer Treat Rev 1990; 17: 261-277.

Seelig MH, Berger MR and Keppler BK. Antineoplastic activity of three ruthenium derivatives against chemically induced colorectal carcinoma in rats, J Cancer Res Clin Oncol 1992; 188: 195-200.

Webster LK, Olver IN, Stokes KH, Sephton RG, Hillcoat BL and Bishop JF. A pharmacokinetic and phase II study of gallium nitrate in patients with non-small cell lung cancer. Cancer Chemother & Pharmacol 2000; 45: 55-58.

Brechbiel MW. Chelated metal ions for therapeutic and diagnostic applications. Exper Biol & med 2001; 226: 627-628.

Veronese I, Giussani A, Cantono MC, de Bartolo D, Roth P and Werner E. Kinetics of systemic rithenium in human blood using a stable tracer. J Radiol Protect 2001; 21: 31-38.

Crul M, van den Bongard HJ, Tibben MM, van Tellingen O, Sava G, Schellens JH and Beijnen JH. Validated method for the determination of the novel organo-rithenium anticancer drug NAMI-A in human biological fluids by Zeeman atomic absorption spectrometry. Fresenius J Anal Chem 2001; 369: 442-445.

Howard JB and Rees DC. Perspectives on non-heme iron protein chemistry. Adv Protein Chem 1991; 42: 199-280.

Barabas K and Faulk WP. Transferrin receptors associate with drug resistance in cancer cells. Biochem Biophys Res Com 1993; 197: 702-708.

Luttropp CA, Jackson JA, Jones BJ, Sohn MH, Lynch RE and Morton KA. Uptake of Gallium-67 in transfected cells on tumors absent or enriched in the transferrin receptors. J Nucl Med 1998; 39: 1405-1411.

Pannccio M, Zalcberg JR, Thompson CH, Leyden JM, SullivanJR, Lichtenstein M and McKenzie IF. Heterogeneity of the human transferrin receptor and use of anti-transferrin receptor antibodies to detect tumors in vivo. Immunol & Cell Biol 1987; 65: 461-472.

Farley J, Loup D, Nelson M, Miller MJ, Taylor R and Gray K. Transferrin in normal and neoplastic endocervical tissues: distribution and receptor expression. Analyst & Quant Cytol & Histol 1998; 20: 238-249.

Sausville EA and Feigal E. Evolving approaches to cancer drug discovery and development at the National Cancer Institute, USA. Annals Oncol 1999; 10: 1287-1291.

Surolia N and Misquith S. Cell surface directed targeting of toxin to human malaria parasite. FEBS Lett 1996; 396:57-61.

Ohno H, Aguilar RC, Fournier M-C, Hennecke S, Cosson P and Boifacirio JS. Interaction of endocytic signals from the HIV-1 envelope glycoprotein complex with members of the adaptor medium chain family. Virology 1997; 238: 305-315.

Woodward JE, Bayer AL and Baliga P. Enhanced allograft survival via simultaneous blockade of transferrin receptor and interleukin-2-receptor. Transplantation 1999; 68: 1369-1376.

Som, P, Oster ZH, Matsui K, Guglielmi G, Persson BR, Pellettieri ML, Srivastrava SC, Richards P, Atkins HL and Brill AB, 97Ru-transferrin uptake in tumor and abscess. Eur J Nucl Med 1983; 8: 491-494.

Lambert JR. Pharmacology of bismuth-containing compounds. Rev Inf Dis 1991; 13(Suppl 8): S691-S695.

Pariente JL, Bordenave L, Bareille R, Ohayon-Courtes C, Baquey C and LeGuillou M. In vitro cytocompatibility of radio-opacifiers used in ureteral endoprothesis. Biomaterials 1999; 20: 523-527.

Krari N, Mauras Y and Allain P. Enhancement of bismuth toxicity by L-cysteine. Res Com Mol Pathol & Pharmacol 1995; 89: 357-364.

Stoltenberg M, Schionning S and Danscher G. Retrograde axonal transport of bismuth: an autometrallographic study. Acta Neuropathol 2001; 101: 123-128.

* cited by examiner

TARGETED DELIVERY OF DRUGS FOR THE TREATMENT OF PARASITIC INFECTIONS

CROSS REFERENCE TO RELATED APPLICATION

This application is a 35 USC § 371 National Phase Entry Application from PCT/US02/11893, filed May 16, 2002, and designating the U.S., which claims priority benefit of U.S. Provisional Application Nos. 60/291,017 filed May 16, 2001 and 60/291,018 filed May 16, 2001. The disclosure of the International Application and the two U.S. Provisional Applications are hereby incorporated by reference.

FIELD OF THE INVENTION

This invention relates generally to the field of bio-affecting materials and, more specifically to bio-affecting materials suitable for treating cells that are infected with a parasite.

BACKGROUND OF THE INVENTION

Protozoa are unicellular eukaryotic organisms that can infect and multiply in mammalian hosts. They may utilize more than one type of host, including insect hosts, during their life cycle. Parasitic protozoa account for a significant portion of all infectious diseases worldwide. Although the majority of protozoan infections occur in developing countries, these infections are seen increasingly in industrialized countries among immigrants and immunosuppressed or immunodeficient individuals. Commonly seen parasitic diseases include malaria, trypanosorriasis, and Chagas disease. The treatment of protozoan infections is problematic due to lack of effective chemotherapeutic agents which traverse the blood brain barrier, excessive toxicity of the therapeutic agents and increasingly widespread resistance to the therapeutic agents. Well known and presently used drugs for treating parasitic infections, caused by protozoa include the drugs melarsopral, eflornithine, chloroquine, quinine, mefloquine, amodiaquine, primaquine, pyrimethamine, sulfadoxine, sulfadiazine, trimethoprim, pentavalent antimony, pentamidine, amphotericin-B, rifampin, metronidazole, ketoconazole, benznidazole, nifurtimox, and halofantrinc.

Two common problems in treatments which involve drugs are drug-toxicity, which debilitates patients, and drug-resistance, which requires more drugs and thus amplifies the problem of drug-toxicity, often resulting in death. One way to solve the problem of drug-toxicity is to deliver drugs so they are targeted only to the infected cells or tissues. Many researchers are working to develop antibodies to deliver drugs, and this approach holds promise, but antibodies are not without problems. For example, they often cross-react with normal tissues, and they can damage blood vessels (e.g., vascular leak syndrome) and cause dangerous allergic reactions (e.g. anaphylaxis).

The treatment of specific cells by the delivery of drugs, including drugs that are toxic to such cells, is not new. U.S. Pat. Nos. 4,886,780; 4,895,714; 5,000,935; and 5,108,987 to Faulk and U.S. Pat. No. 4,590,001 to Stjernholm et. al., describe cytotoxic. or radioimaging materials conjugated to proteins, mainly to transferrin, as treatments for cancerous cells or for imaging cancerous cells.

It is known that stressed cells, such as, for example, human cells hosting a parasitic infection, call for an increased delivery of nutrients, such as iron, by presenting an increased number of receptors for nutrient carriers, such as transferrin in the case of iron. The increase in receptors for nutrient carriers in stressed cells is known to be relatively constant and orders of magnitude greater in number than in unstressed cells, which are known to show receptors intermittently and in relatively smaller numbers. The publications listed above, and others, disclose taking advantage of the increased number of receptors, especially for transferrin, presented by cancer containing cells to deliver imaging materials or drugs or both to the stressed cell.

No single study has asked if all stressed cells have up regulated transferrin receptors, or if all normal cells have down regulated transferrin receptors, but data from many quarters suggest that all normal cells have down regulated transferrin receptors. For example, immature erythrocytes (i.e., normoblasts and reticulocytes) have transferrin receptors on their surfaces, but mature erythrocytes do not (Lesley J, Hyman R, Schulte R and Trotter J. Expression of transferrin receptor on murine hematopoietic progenitors. Cell Immunol 1984; 83: 14–25). Circulating monocytes also do not have up regulated transferrin receptors (Testa U, Pelosi E and Peschle C. The transferrin receptor. Crit Rev Oncogen 1993; 4: 241–276), and macrophages, including Kupffer cells, acquire most of their iron by a transferrin-independent method of erythrophagocytosis (Bothwell T A, Charlton R W, Cook J D and Finch C A. *Iron Metabolism in Man*, Blackwell Scientific, Oxford, 1979). In fact, in vivo studies indicate that virtually no iron enters the reticuloendothelial system from plasma transferrin (for review, see Ponka P and Lok C N. The transferrin receptor: role in health and disease. Int J Biochem Cell Biol 1999; 31: 1111–1137.). Macrophage transferrin receptors are down regulated by cytokines such as gamma interferon (Hamilton T A, Gray P W and Adams D O. Expression of the transferrin receptor on murine peritoneal macrophages is modulated by in vitro treatment with interferon gamma Cell Immunol 1984; 89: 478–488.), presumably as a mechanism of iron-restriction to kill intracellular parasites (Byrd T F and Horowitz M A. Interferon gamma-activated human monocytes downregulate transferrin receptors and inhibit the intracellular multiplication of *Legionella. pneumophila* by limiting the availability of iron J Clin Invest 1989; 83: 1457–1465.).

In resting lymphocytes, not only are transferrin receptors down regulated, but the gene for transferrin receptor is not measurable (Kronke M, Leonard W, Depper. J M and Greene W C. Sequential expression of genes involved in human T lymphocyte growth and differentiation. J Exp Med 1985; 161: 1593–1598). In contrast, stimulated lymphocytes up-regulate transferrin receptors in late $G_1$ (Galbraith R M and Galbraith G M. Expression of transferrin receptors on mitogen-stimulated human peripheral blood lymphocytes: relation to cellular activation and related metabolic events. Immunology 1983; 133: 703–710). Receptor expression occurs subsequent to expression of the c-myc proto-oncogene and following up-regulation of IL-2 receptor (Neckers L M and Cossman J. Transferrin receptor induction in mitogen-stimulated human T lymphocytes is required for DNA synthesis and cell division and is regulated by interleukin 2. Proc Nat Acad Sci USA 1983; 80: 3494–3498.), and is accompanied by a measurable increase in iron-regulatory protein binding activity (Testa U, Kuhn L, Petrini M, Quaranta M T, Pelosi E and Peschle C. Differential regulation of iron regulatory element-binding protein(s) in cell extracts of activated lymphocytes versus monocytes-macrophages. J Biol Chem 1991; 266: 3925–3930), which stabilizes transferrin receptor mRNA (Seiser C, Texieira S and Kuhn L C. Interleukin-2-dependent transcriptional and post-transcriptional regulation of transferrin receptor-mRNA. J Biol Chem 1993; 268: 13,074–13,080.). This is true for both T and B lymphocytes (Neckers L M, Yenokida G and James S P. The role of the transferrin receptor in human B lymphocyte activation. J Immunol 1984; 133: 2437–2441), and is an IL-2-dependent response (Neckers L M and Trepel J B. Transferrin-receptor expression and the control of cell growth Cancer Invest 1986; 4: 461–470).

Malaria

Approximately 40% of the world's population are at risk for malaria. That is, in excess of 2000 million people in about 100 countries are at risk (Gilles, 1991, World Health Organization, Geneva). Particularly affected are children in developing countries (Greenwood et al., Trans Soc Trop Med Hyg 1987; 81:478). For example, a million children die of malaria every year in sub-Saharan Africa (World Health Organization, 1974, Technical Report Series No. 537). The rise of travel, trade and tourism also has extended malaria into developed countries (Greenberg & Lobel, Ann Intern Med 1990; 113:326). These social and economic problems are compounded by the complexities of vector control and the problematic development of an effective malaria vaccine (Graves & Gelband, Cochrane Database of Systematic Reviews CD000129, 2000). Thus, anti-malarial drugs remain the bulwark of defense against malaria, but this is being eroded by the spreading emergence of drug resistant strains of *Plasmodiurn falciparurn*, causing safe, widely available and inexpensive drugs like chloroquine to be increasingly less effective (Clyde, Epidemiol Rev 1987; 9:219). Taken together, these observations-indicate a pressing need for new drug strategies in the war on malaria The present invention provides a new strategy for the design of anti-malarial drugs.

The *Plasmodium falciparum* parasite reproduces rapidly within red blood cells of its host. Red cells are invaded by the merozoite stage of the parasite, which matures into the trophozoite stage and sufficiently replicates its DNA to produce 32 daughter cells within 48 hours. Like all developing cells (Richardson & Ponka, Biochim Biophys Acta 1997; 1331:1), developing plasmodia require iron to promote the function of key enzymes, such as ribonucleotide reductase for DNA synthesis (Chitambar et al., Biochem J 2000; 345:681), and iron-dependent enzymes for pyrimidine synthesis, $CO_2$ fixation and mitochondrial electron transport (Mabeza et al., Acta Haematol 1996; 95:78). The importance of iron in plasmodial development has been demonstrated in both in vitro Cabantchik et al., Acta Haematol 1996; 95:70) and in vivo (Pollack et al., Proc Soc Exp Biol Med 1987; 184:162) models in which growth of parasites is inhibited by iron chelation. The most widely studied iron chelator is deferoximine, which is a siderophore or chelator that tightly (i.e., affinity of $10^{31}$/M) binds iron (Peto & Thompson, Br J Haematol 1986; 63:273). Clinical studies of Zambian children with advanced cerebral malaria (e.g., comatose) have revealed that patients treated with a standard program of anti-malarial therapy plus deferoxamine (100 mg/kg/day) recovered more rapidly than patients who received the same program of anti-malarial therapy without deferoxarine (Gordeuk et al., N Engl J Med 1992; 327:1473).

In light of the key role played by iron in the growth and development of plasmodia, much research has focused on how plasmodia obtain iron, and whether the parasites can be killed by drugs that interfere with the metabolic pathways that are used to acquire iron. Conceptually, plasmodia can obtain iron either from within the red blood cells in which they reside, or from the patient's transferrin, which is the normal protein in blood that carries iron (Ponka & Lok, Int J Biochem Cell Biol 1999; 31:1111). There is little doubt that plasmodia are capable of obtaining iron from red blood cells (Hershko & Peto, J Exp Med 1988; 168:375). In order to obtain iron from the patient's transferrin, there must be transferrin receptors on red blood cells, but normal adult red blood cells do not manifest transferrin receptors (Richardson & Ponka, Biochim Biophys Acta 1997; 1331:1). However, malaria infected red blood cells bind transferrin (Pollack & Fleming, Br J Haematol 1984; 58:289), and data have been produced that have identified 102 kD (Haldar et al., Proc Natl Acad Sci USA 1986; 83:8565) and 93 kD (Rodriguez & Jungery, Nature 1986; 324:388) transferrin receptors in the plasma membranes of red blood cells infected with *Plasmodium falciparum*. Although these observations have been challenged (Pollack & Schnelle, Br J Haematol 1988; 68: 125), subsequent experiments have shown that the receptors are functional, inasmuch as they have been used to deliver an anti-plasmodial toxin to infected red cells, and such delivery was inhibited by antibody to transferrin (Surolia & Misquith, FEBS Letters 1996; 396:57).

Trypanosomiasis

Trypanosomiasis is a parasitic infection caused by trypanosomes, which are protozoans that are passed to human beings by the bite of an infected tsetse fly (Smith et al., Brit Med Bull 1998; 54:341). When introduced into patients, trypanosomes proliferate in blood and lymphatics, which is the first stage of disease; the second stage of disease develops when parasites traverse the blood-brain-barrier and cause neurological damage and lethargy, commonly known as sleeping sickness (Beutivoglio et al., Trends Neurosci 1994; 17:325). If untreated, trypanosomiasis in both humans and animals is a fatal disease (New York Times, May 21, 2000).

There are two clinical forms of infection that are caused by different trypanosome subspecies. First, *Trypanosoma brucei* gambiense causes a chronic disease that takes several years to reach advanced stage; second, *Trypanosoma brucei* rhodesiense causes an acute disease that is fatal within weeks; Both diseases are endemic in Africa, and infections with *Trypanosoma brucei* gambiense currently are epidemic, placing at risk 60 million people inhabiting 36 sub-Saharan countries (Barrett, Lancet 1999; 353:1113). In addition, trypanosomiasis is limited neither to Africa (Dissanaike, Celyon Med J 2000; 45:40) nor to humans (Karnau et al., Prevent Vet Med 2000; 44:231), and the economic impact of these diseases profoundly impact national economies (Bauer et al., Trop. Animal Hlth & Prod 1999; 31:89).

Diagnostic approaches to trypanosomiasis have been designed to identify the stage of disease in patients, for early infections limited to blood and lymphatics can be treated with less toxic drugs than later infections involving the central nervous system (Dumas & Buiteille, Med Trop 1997; 57:65). There are currently two drugs for treatment of central nervous system infections (i.e., sleeping sickness). The least expensive, most available and most toxic is melarsopral, which is an arsenical drug that induces a fatal encephalopathy in 5–7% of recipients (Harrison et al., Am J Trop Med Hyg 1997; 56:632). These problems are compounded by drug resistance, low response rates and relapse rates as high as 10% (Pepin & Milard, Adv Parasitol 1994; 33:1). A less toxic, more expensive and difficult to acquire alternative to melarsopral is eflornithine, which is an ornithine decarboxylase inhibitor that impedes polyamine synthesis (Sjoerdsma & Schechter, Lancet 1999; 354:254), but this molecule presently is being marketed as an expensive anti-cancer drug.

There also currently are two drugs available for treatment of early stage infections. One of these, pentamidine, was developed in 1941, and the other, suramin, was developed in 1920. Pentamidine also is effective in *Pneumocystis carinii* infections common in AIDS patients, and it is about 4-fold more expensive than suramin, which for the moment is used only in trypanosomiasis. There are other compounds with trypanocidal activity (Enanga et al., Trop Med Int Health 1998; 3:736), but most of these do not cross the blood-brain-barrier and thus are of limited usefulness in infections of the central nervous system.

The targeted delivery of drugs has the advantage of increasing efficacy while using less drug, thereby decreasing toxicity and causing less damage to normal cells, all of which effectively decrease costs and increase the quality of patient care. Targeted delivery also avoids drug-resistance, which is activated by the non-specific entrance of drugs into cells (Marbeuf-Gueye C, Ettori D, Priebe W, Kozlowski H and Gamier-Suillerot A. Correlation between the kinetics of anthracycline uptake and the resistance factor,in cancer cells expressing the multidrug resistance protein or the P-glyco-protein. Biochem Biophy Acta 1999; 1450: 374–384). Because transferrin-drug conjugates enter cells specifically by employing a receptor-specific pathway (Klausner R D, vanReuswoude J, Ashwell G, Kempf C, Schechter A N, Dean A and Bridges K. Receptor-mediated endocytosis of transferrin in K562 cells. J Biol Chem, 1983; 258: 4715–4724.; Berczi A,.Ruthner M, Szuts V, Fritzer M, Schweinzer E and Goldenberg H. Influence of conjugation of doxorubicin to transferrin on the iron uptake by K562 cells via receptor-mediated endocytosis. Euro J Biochem 1993; 213: 427–436.), they are trafficked around drug-resistance mechanisms, such as efflux pumps in resistant cells.

There exists an unfulfilled need for an inexpensive and effective agent for selectively targeting and eliminating cells diseased by protozoan parasitic invasion

SUMMARY OF THE INVENTION

The present invention provides a material for treating parasitic protozoa infections such as malaria, trypanosomia-sis, and Chagas disease (which can be caused by *Trypano-somo cruzi*). The material is a conjugate comprising a targeting agent such as transferrin or transcobalamin and an anti-protozoan drug. Suitable drugs include but are not limited to doxorubicin, deferoxamine, melarsopral, eflorni-thine, pentamidine, quinine, mefloquine, amodiaquine, pri-maquine, pyrimethalrnme, sulfadoxine, sulfadiazine, trime-thoprim, pentavalent antimony, amphotericin B, rifamnpin, metronidazole, ketoconazole, benznidazole and nifurtimox, and suramin. The present invention also provides a method for treating patients infected with a protozoa and a composition containing the conjugate.

DETAILED DESCRIPTION OF THE INVENTION

The above discussed needs are filled by a conjugate for treating infected cells, especially cells stressed by a protozoan infection, that, in one embodiment includes a targeting agent that is attracted to a receptor that is expressed in higher numbers or more frequently by cells infected by a protozoa than by normal uninfected cells, and an anti-protozoan drug.

The targeting agent can be any material that is attracted to receptors on cells that present in higher numbers Or more frequently when a cell is stressed from a protozoan infection. Preferably, the targeting agent is transferrin.

Attachment of the drug to the targeting agent may be by any mechanism that prevents their separation, at least until after the targeting agent has been positioned in the corresponding receptor. Presently, the best known mechanism for attachment for a transferrin-doxorubicin conjugate is a glutaraldehyde linker, but the linker can be any material useful for the targeting agent/drug combination in question.

Technical details of the conjugation procedure can vary, but the requirement of any procedure is to prepare defined conjugates that are (a) active in binding and killing experiments with protozoan infected cells, and that (b) do not bind or kill significant numbers of normal cells. In light of these requirements, when transferrin is used as the targeting agent and doxorubicin is used as the anti-protozoan drug, the preferred method for preparing the conjugates according to the present invention is the following process.

The synthesis of large amounts of homogeneous transferrin-doxorubicin conjugates with predetermined molecular ratios was done stoichiometrically by employing the only amino group of doxorubicin (DOX), which is at the 3' amino position, to react with one of the two reactive groups on glutaraldehyde (GLU). Thus, the first step was drop-wise addition of a saline solution of DOX into a saline solution of GLU containing a solvent such as DMSO or another suitable cryopreservative, to a final concentration of a 1:1 molar ratio of DOX-to-GLU. The resulting solution of DOX-GLU was stirred three hours at room temperature in the dark.

The molarities of DOX and GLU were the same in the above reaction in order to produce a final solution of DOX-GLU that contains neither free DOX nor free GLU. However, there is the possibility of free GLU in solution if one GLU reacts with two DOX to produce DOX-GLU-DOX, but this possibility is minimized by the mass action kinetics generated by drop-wise addition of monovalent DOX into the solution of bivalent GLU. The volumes of these reactants are not restricted, so large amounts of homogeneous DOX-GLU can be prepared.

The second step in the conjugation reaction was drop-wise addition of DOX-GLU into a saline solution of transferrin (TRF). The TRF can be either iron-free (apo-transferrin) or iron-saturated (holo-transferrin). The desired molar ratio of DOX to TRF was obtained by appropriately adjusting the volume of TRF. The resulting solution of TRF-GLU-DOX was stirred for 20 hours at room temperature in the dark. Unlike the reaction of DOX with GLU, the reaction of DOX-GLU with TRF is not restricted to one binding site, for the GLU component of DOX-GLU can react with any one of several epsilon-amino lysine groups in the TRF molecule.

The number of DOX molecules bound to TRF was determined in the second step. For example, if the starting ratio of DOX-GLU to TRF was 7.2:1.0, the final solution of TRF-GLU-DOX would have contained 2.5 molecules of DOX per molecule of TRF. However, if the starting ratio of DOX-GLU to TRF was 4.0:1.0, the final solution of TRF-GLU-DOX would have contained 1.4 molecules of DOX per molecule of TRF. Similarly, if the starting ratio of DOX-GLU to TRF was 2.5:1.0, the final solution of TRF-GLU-DOX would have contained 0.9 molecules of DOX per molecule of TRF. In this way, large amounts of TRF-GLU-DOX with predetermined ratios of DOX-to-TRF can be provided according to the need.

One skilled in the art will appreciate that there may be unreacted linker and a small amount of unintended constructions, such as DOX-GLU-DOX in the reaction, product and that it will be desirable to optimize the reaction product by removing them. Ethanolamine or another substance suitable for scavenging any excess linker may be added to the reaction product, followed by centrifugation and dialysis, may be used to remove excess GLU and such unintended constructions. Although reactions with DOX and TRF theoretically consume all of the GLU, ethanolamine was added to the final reaction mixture to bind any available GLU. This reaction was allowed to continue for 30 minutes in the dark. The final solution was centrifuged at 2000 rpm for 10 minutes, dialyzed twice for 6 hours in a 100-fold excess of saline and three times in the same excess of Hepes buffered saline, and the resulting TRF-GLU-DOX conjugates were ready for use.

Biochemical Characterization of the Conjugates:

By using HPLC and polyacrylamide gel electrophoresis, the homogeneity of TRF-GLU-DOX conjugates can be determined. Also, by using spectrophotometry, the molecular ratio of DOX-to-TRF can be determined. These techniques repeatedly have revealed a consistent homogeneity of the TRF-GLU-DOX conjugates. In addition, chromatography is not required in the preparation of these conjugates, because there are no aggregates or fragments. This allows for the preparation of large volumes of homogeneous transferrin-drug conjugates, which increases yields and decreases costs.

The expenses caused by losses of TRF and DOX in other types of transferrin-drug conjugates have been an impediment to their use. For example, yields of DOX and TRF are decreased by using procedures such as thiolation that alter the drug and/or protein. Yields also are decreased by using solvent systems and by chromatography used to prepare acid-stable and acid-labile linkages. The GLU bond between DOX and TRF is acid-stable, and yields of useful conjugates prepared according to this invention are high Indeed, compared to other procedures, the yield for useful conjugate is increased 5-fold.

None of the previously known approaches to the preparation of transferrin-doxorubicin conjugates are capable of producing large amounts of homogeneous conjugates with predetermined ratios of the number of drug molecules per molecule of transferrin. In addition, the known approaches employ chromatography to eliminate aggregates and to harvest fractions that are enriched in homogeneous conjugates. These procedures decrease yields, increase costs, and lack the ability to predetermine molecular ratios.

After the conjugates are isolated, they can optionally be characterized by polyacrylamide gel electrophoresis to determine their molecular weight, and the number of drug molecules per protein molecule can be determined. Experience with drug-protein conjugates in other systems has shown that a functional drug:protein ratio is 0.1–4.0 molecules of drug per molecule of protein (Berczi et al., Arch Biochem Biophy 1993; 300:356), recent unpublished data suggest that lower conjugation numbers are still significantly cytotoxic, while higher conjugation numbers (e.g., >4.0) tend to be associated with unstable conjugates. Other steps in the characterization of the conjugates are to (a) determine if the conjugates bind to transferrin receptors on the surface of infected cells and not uninfected cells, and (b) determine if the conjugates kill protozoan infected cells and not uninfected cells. The binding studies can be done by using flow cytometry, and the killing studies can be done by using microculture techniques to determine the concentration of free drug required to kill 50% of a culture of infected cells compared to the concentration of drug in the drug-protein conjugate required to kill the same number of infected cells. Experience with drug-protein conjugates in other systems indicates that approximately 10-fold more free drug compared to the drug in drug-protein conjugates should be required to kill the same number of infected cells. For example, the dosage of a conjugate of transferrin-doxorubicin is expected to be between 0.5–50 mg per 28 day period for a 150 pound (68 kg) person The dosage can be administered as smaller doses at varying intervals during the 28 day period. For a conjugate to be efficacious, preferably it should kill none or only a minimum of uninfected cells.

Treatment of Malaria

Since drug resistance (World Health Org., Technical Report Series No 692, 2000) and drug toxicity (Winstanley, J Roy Col Phy London 1998; 32:203) are major problems in the treatment of malaria, the aim of the present invention is to provide a ligand-receptor method for the targeted delivery of anti-malarial drugs designed to utilize the pathways employed by plasmodia to acquire iron In one embodiment, the ligand is human transferrin, the receptor is plasmodial transferrin receptor, and the drug is either the cytotoxic drug doxorubicin which also is an iron chelator (Myers, Seminars Oncol 1998; 25:10); or the iron-chelating siderophore deferoxamine (also known as desferrioxamine or Desferal). Deferoxarnine is a hydroxamate-based hydrophilic chelator of iron (Tsafack et al., J Lab Clin Med 1996; 127:574). The molecule has a terminal $NH_2$ that has been derivatized with molecules such as nitrobezyl-diazole and N-methylanthranile without reducing its property of iron chelation (Loyevsky et al., J Clin Invest 1993; 91:218).

Treatment of Trypanosomiasis

A carrier is needed that could transport trypanocidal compounds across the blood-brain-barrier. The normal plasma protein transferrin has been shown to accomplish this task by means of interacting with transferrin receptors on endothelial cells that compose the microcirculation of the blood-brain-barrier (Broadwell et al., Exp Neurol 1996; 142:47). For example, a conjugate of transferrin with nerve growth factor has been shown to be transported from blood into the brain (Li et al., J Natural Tox 2000; 9:73), and the object of the present invention is to provide conjugates of trypanocidal drugs with transferrin that can be transported from blood across the blood-brain-barrier into the central nervous system, thereby providing effective therapy for both early and late stages of trypanosomiasis.

In addition to being an effective transporter of trypanocidal drugs across the blood-brain-barrier, transferrin can be targeted to transferrin receptors present on trypanosomal plasma membranes (Borst et al., Science 1994; 264:1872). Like human transferrin receptors, trypanosomal receptors are regulated post-transcriptionally by iron (Fast et al., Biochem J 1999; 342:691). Each trypanosome contains about 3000 receptors, which are heterodimers linked by a glycosylphosphatidylinositol anchor to the plasma membrane where they concentrate in flagellar pockets, among a sea of variant surface glycoprotein (Borst & Fairlamb, Ann Rev Microbiol 1998; 52:745). Trypanosomes require iron, which they obtain from the transferrin of their host (Schell et al., EMBO J 1991; 10:1061). Since they can thrive in many different mammalian hosts, and since transferrins differ in different mammals, trypanosomes have about 20 gene copies of transferrin receptors, which allows them to produce a high-affinity receptor to bind and internalize host transferrins, whether they be in animals or human patients (Bitter et al., Nature 1998; 391:499). Thus, intravenously administered trypanocidal drug conjugates of transferrin circulate throughout the body, including the central nervous system, where they are bound by trypanosomal transferrin receptors and exercise their trypanocidal properties.

The present invention is a drug-protein conjugate which can be used for the targeted delivery of a cytotoxic drug to trypanosomes in infected patients, whether they are in early or late stages of disease, and regardless of which Trypanosoma species with which they are infected. Targeted delivery of drugs is possible in this invention because the preferred protein in the drug-protein conjugate is transferrin, which is relevant because trypanosomes have transferrin receptors on their surfaces (Bitter et al., Nature 1998; 391:499). In addition, the drug in the drug-transferrin corrugate can be a known trypanocidal agent, or cytotoxic drug such as doxorubicin. While being present on the surfaces of cancer cells (Yeh et al., Vox Sang 1984; 46:217), transferrin receptors usually are not present on the surface of normal, adult, resting cells (Berczi et al., Arch Biochem Biophy 1993; 300:356). Thus, most normal cells in trypanosomiasis patients will not be affected, and the only cells to be eliminated by cytotoxic transferrin conjugates will be the trypanosomes, whether they are in blood, lymph or the central nervous system.

One way to illustrate targeted drug delivery to trypanosomes in patients is to focus on the use of transferrin, which carries iron in the blood. Transferrin can be obtained by isolation from blood plasma, from commercial suppliers, or from recombinant technology (Ali et al., J Biol Chem 1999; 274;2406 6). To form the drug-protein conjugate, transferrin molecules must be modified in such a way as to prepare them to be coupled with a trypanocidal or cytostatic drug. The drug can be an arsenical such as melarsopral, a cytotoxic antibiotic such as doxorubicin or an inhibitor of polyarnine synthesis such as eflomithine, but any compound can be used, including plant toxins such as ricin, and bacterial mutant toxins such as modified diphtheriatoxin (Laske et al., Nature Med 1997; 41:1039).

Several coupling processes such as glutaraldehyde coupling (Yeh & Faulk, Clin Immunol Immunopathol 1984; 32:1), disulfide coupling (Sasaki et al., Jap J Can Res 1993; 84: 191) or benzyl hydrazine coupling (Kratz et al., J Pharm Sci 1998; 87: 338) have been used to couple transferrin with other molecules. The wide variety of coupling procedures allows the conjugation of a broad range of drugs to transferrin, resulting in either permanent or dissociable bonding of the drugs with the transferrin molecule (Barabas et al., J Biol Chem 1992; 267:9437). Following the coupling reaction, drug-protein conjugates can be separated from uncoupled drug and free protein, if necessary by using chromatographic procedures or selective dialysis.

While the present invention has been described in relation to transferrin being the delivery protein, it is known that other proteins exist in the body which are capable of binding to receptor sites on infected cells. If the receptor site is activated in infected cells, and is inactive in uninfected cells, then any protein or other compound which binds to such a receptor site can be used to deliver the drugs used in the present invention. One example of such a binding protein is transcobalamin, which delivers vitamins, especially vitamin B12, to transcobalamin receptors on cells in the human body (Seetheram, Ann Rev Nutr 1999; 19:173). Other examples include but are not limited to ceruloplasmin, vitamin binding proteins, hormones, cytokines, low density lipoproteins, and growth factors.

The conjugates according to the present invention are administered to an animal in an effective amount In treating protozoan infections, an effective amount includes an amount effective to reduce the amount of protozoa The dosage for the conjugates can be determined taking into account the age, weight and condition of the patient and the pharmacokinetics of the anti-protozoan agent. The amount of the conjugate required for effective treatment will be less than the amount required using the anti-protozoan agent alone and depends upon the anti-protozoan agent used. For example, the dosage of a conjugate of transferrin-doxorubicin is expected to be between 0.5–50 mg for a 150 pound (68 kg) person. The dosage can be administered as smaller doses at varying intervals and repeated if necessary.

The pharmaceutical compositions of the invention can be administered by a number of routes, including but not limited to orally, topically, rectally, ocularly, vaginally, by pulmonary route, for instance, by use of an aerosol, or parenterally, including but not limited to intramuscularly, subcutaneously, intraperitoneally, intra-arterially or intravenously. The compositions can be administered alone, or can be combined with a pharmaceutically-acceptable carrier or excipient according to standard pharmaceutical practice. For the oral mode of administration, the compositions can be used in the form of tablets, capsules, lozenges, troches, powders, syrups, elixirs, aqueous solutions and suspensions, and the like. For parenteral administration, sterile solutions of the conjugate are usually prepared, and the pHs of the solutions are suitably adjusted and buffered. For intravenous use, the total concentration of solutes should be controlled to render the preparation isotonic. For ocular administration, ointments or droppable liquids may be delivered by ocular delivery systems known to the art such as applicators or eye droppers. For pulmonary administration, diluents and/or carriers will be selected to be appropriate to allow the formation of an aerosol. It is preferred that the conjugate of the present invention be administered parenterally, i.e. intravenously or intraperitoneally, by infusion or injection.

As used in the present document, the term "substantially homogeneous conjugates" means that the conjugates can be used without further purification to remove protein dimers, polymers or aggregates. In other words, little or no protein dimers, polymers or aggregates are present.

Preferred embodiments of the present invention are described below. It will be apparent to those of ordinary skill in the art after reading the following description that modifications and variations are possible, all of which are intended to fall within the scope of the claims.

EXAMPLE 1

Preparation of Conjugates

The synthesis of large amounts of homogeneous transferrin-doxorubicin conjugates with predetermined molecular ratios was done stoichiometrically by employing the only amino group of doxorubicin (DOX), which is at the 3' amino position, to react with one of the two reactive groups on glutaraldehyde (GLU). The first step was to add GLU drop-wise to DMSO in an ice cold water bath. Next was the drop-wise addition of a saline solution of DOX into a saline solution of GLU+DMSO to a final concentration of a 1:1 molar ratio of DOX-to-GLU. The resulting solution of DOX-GLU was stirred three hours at room temperature in the dark.

The molarities of DOX and GLU were the same in the above reaction in order to produce a final solution of DOX-GLU that contains neither free DOX nor free GLU. However, there is the possibility of free GLU in solution if one GLU reacts with two DOX to produce DOX-GLU-DOX, but this possibility is minimized by the mass action kinetics generated by drop-wise addition of monovalent DOX into the solution of bivalent GLU. The volumes of these reactants are not restricted, so large amounts of homogeneous DOX-GLU can be prepared.

The second step in the conjugation reaction was drop-wise addition of DOX-GLU into a saline solution of transferrin (TRF). The TRF can be either iron-free (apo-transferrin) or iron-saturated (holo-transferrin). The desired molar ratio of DOX to TRF was obtained by appropriately adjusting the volume of TRF. The resulting solution of TRF-GLU-DOX was stirred for 20 hours at room temperature in the dark. Unlike the reaction of DOX with GLU, the reaction of DOX-GLU with TRF is not restricted to one binding site, for the GLU component of DOX-GLU can react with any one of several epsilon-amino lysine groups in the TRF molecule.

The number of DOX molecules bound to TRF was determined in the second step. For example, if the starting ratio of DOX-GLU to TRF was 7.2:1.0, the final solution of TRF-GLU-DOX would have contained 2.5 molecules of DOX per molecule of TRF. However, if the starting ratio of DOX-GLU to TRF was 4.0:1.0, the final solution of TRF-GLU-DOX would have contained 1.4 molecules of DOX per molecule of TRF. Similarly, if the starting ratio of DOX-GLU to TRF was 2.5:1.0, the final solution of TRF-GLU-DOX would have contained 0.9 molecules of DOX per molecule of TRF. In this way, large amounts of TRF-GLU-DOX with predetermined ratios of DOX-to-TRF can be provided according to the need.

In an optimization of the production of the conjugate, ethanolamnine is added, followed by centrifugation and dialysis. Although reactions with DOX and TRF theoretically consume all of the GLU, ethanolamine was added to the final reaction mixture to bind any available GLU. This reaction was allowed to continue for 30 minutes in the dark. The final solution was centrifuged at 2000 rpm for 10 minutes, dialyzed twice for 6 hours in a 100-fold excess of saline and three times in the same excess of Hepes buffered saline, and the resulting TRF-GLU-DOX conjugates were ready for use.

The invention claimed is:

1. A method for selectively treating a cell infected with a protozoa, comprising
   administering to said cell an anti-protozoan effective amount of a conjugate containing a protozoan infected cell targeting agent and an anti-protozoan drug, wherein said anti-protozoan drug is selected from the group consisting of an apoptosis inducing compound, a cytotoxic antibiotic, an alkylating agent, a plant toxin, and a bacterial mutant toxin, and wherein said protozoan infected cell targeting agent is selected from the group consisting of transferrin and transcobalamin.

2. The method according to claim 1, wherein said anti-protozoan drug is selected from the group consisting of doxorubicin, deferoxamine, melarsopral, eflornithine, pentamidine, quinine, mefloquine, amodiaquine, primaquine, pyrimethamine, sulfadoxine, sulfadiazine, trimethop rim, pentavalent antimony, amphotericin B, rifampin, metronidazole, ketoconazole, benznidazole, nifurtimox, suramin, ricin, and choloroquine.

3. The method according to claim 1, wherein said protozoan infected cell targeting agent is transferrin.

4. The method according to claim 2, wherein said protozoa is selected from the group consisting of Plasmodia species and trypanosomes.

5. A method for treating a patient infected with a protozoa, comprising administering to said patient an effective amount of a conjugate containing a protozoan infected cell targeting agent and an anti-protozoan drug, wherein said anti-protozoan drug is selected from the group consisting of an apotosis inducing compound, a cytotoxic antibiotic, an alkyating agent, a plant toxin, and a bacterial mutant toxin, and wherein said protozoan infected cell targeting agent is selected from the group consisting of transferrin and transcobalamin.

6. The method according to claim 5, wherein said protozoa is selected from the group consisting of Plasmodia species and trypanosomes.

7. A pharmaceutical composition suitable for treating protozoan infections comprising a conjugate and a carrier, wherein said conjugate comprises a protozoan infected cell targeting agent and an anti-protozoan drug selected from the group consisting of melarsopral, eflornithine, pentamidine, quinine, mefloquine, amodiaquine, primaquine, pyrimethamine sulfadoxine, sulfadiazine, trimethoprim, pentavalent antimony, metronidazole, ketoconazole, benznidazole, nifurtimox, suramin, ricin, and choloroquine, and wherein said protozoan infected cell targeting agent is selected from the group consisting of transferrin and transcobalamin.

8. The composition according to claim 7, further comprising an unconjugated anti-protozoan drug.

9. The composition according to claim 7, wherein said targeting agent is transferrin.

10. A substantially homogeneous conjugate comprising a targeting agent and an anti-protozoan drug wherein said anti-protozoan drug is selected from the group consisting of melarsopral, eflornithine, pentamidine, quinine, mefloquine, amodiaquine, primaquine, pyrimethamine, sulfadoxine, sulfadiazine, trimethoprim, pentavalent antimony, metronidazole, ketoconazole, benznidazole, nifurtimox, suramin, ricin and choloroquine, and wherein said targeting agent is selected from the group consisting of transferrin and transcobalamin.

11. The conjugate according to claim 10, wherein said targeting agent is transferrin.

12. A reagent kit for determining the susceptibility of protozoan infected cells to anti-protozoan drugs, comprising two or more conjugates each containing a protein targeting agent and an anti-protozoan drug, wherein said conjugates have different anti-protozoan drugs, and wherein at least one anti-protozoan drug is selected from the group consisting of melarsopral, eflornithine, pentamidine, quinine, mefloquine, amodiaquine, primaquine, pyrimethamine, sulfadoxine, sulfadiazine, trimethoprim, pentavalent antimony, amphotericin B, rifampin, metronidazole, ketoconazole, benznidazole, nifurtimox, suramin, ricin, and choloroquine, and wherein said protein targeting agent is selected from the group consisting of transferrin and transcobalamin.

13. A method for making a conjugate having a predetermined anti-protozoan drug: protein ratio, comprising
   a) adding a solution of an anti-protozoan drug dropwise to a linker molecule solution to link each anti-protozoan drug molecule to one linker molecule in a drug/linker combination; and
   b) reacting the drug/linker combination with a protein to produce a conjugate having a predetermined anti-protozoan drug: protein ratio, wherein said protein is selected from the group consisting of transferrin and transcobalamin and wherein said anti-protozoan drug is selected from the group consisting of melarsopral, eflornithine, pentamidine, quinine, mefloquine, amodiaquine, primaquine, pyrimethamine, sulfadoxine, sulfadiazine, trimethoprim, pentavalent antimony, metronidazole, ketoconazole, benznidazole, nifurtimox, suramin, ricin, choloroquine, and deferoxamine.

14. The method according to claim 13, further comprising scavenging any excess linker.

15. The method according to claim 13, wherein said linker is selected from the group consisting of glutaraldehyde, benzoyl hydrazone, maleinimide and N-hydroxysuccinimide.

* * * * *